United States Patent
Muldoon et al.

(10) Patent No.: US 12,161,815 B2
(45) Date of Patent: Dec. 10, 2024

(54) MEDICAL DEVICE HANDLE FOR ARTICULATION OF A CATHETER

(71) Applicant: Creganna Unlimited Company, Galway (IE)

(72) Inventors: Damian Muldoon, Galway (IE); Brian Murphy, Galway (IE); Shane Ward, Galway (IE); Diarmuaid Quaid, Galway (IE)

(73) Assignee: Creganna Unlimited Company, Galway (IE)

( * ) Notice: Subject to any disclaimer, the term of this patent is extended or adjusted under 35 U.S.C. 154(b) by 52 days.

(21) Appl. No.: 17/009,447

(22) Filed: Sep. 1, 2020

(65) Prior Publication Data

US 2021/0060297 A1 Mar. 4, 2021

(30) Foreign Application Priority Data

Sep. 3, 2019 (EP) .................................... 19195025

(51) Int. Cl.
*A61M 25/01* (2006.01)

(52) U.S. Cl.
CPC .... *A61M 25/0136* (2013.01); *A61M 25/0113* (2013.01); *A61M 25/0147* (2013.01)

(58) Field of Classification Search
CPC .......... A61M 25/0147; A61M 25/0136; A61M 25/0113
See application file for complete search history.

(56) References Cited

U.S. PATENT DOCUMENTS

| 5,185,004 A | * | 2/1993 | Lashinski | A61M 25/0136 |
| | | | | 604/533 |
| 5,327,905 A | * | 7/1994 | Avitall | A61B 18/1492 |
| | | | | 606/45 |

(Continued)

FOREIGN PATENT DOCUMENTS

| JP | 2018029795 A | 3/2018 | | |
| WO | WO-9101772 A1 | * | 2/1991 | ........ A61M 25/0147 |

(Continued)

OTHER PUBLICATIONS

Extended European Search Report, dated Mar. 10, 2020, 8 pages.

(Continued)

*Primary Examiner* — Jason E Flick
*Assistant Examiner* — Adam J. Cermak
(74) *Attorney, Agent, or Firm* — Barley Snyder (57) ABSTRACT

A medical device handle for articulation of a catheter includes a housing having a cylindrical shape, a control element at least partly encompassed by the housing, the control element having a pair of cross-cut threads cross-cut in opposing directions around a longitudinal axis of the medical device handle, and a pair of pull wire mounting elements each having a mounting thread engaging with one of the cross-cut threads. The control element is mechanically coupled to each of the pull wire mounting elements via the cross-cut threads and the mounting threads without any additional gear in between. A rotation of the control element around the longitudinal axis moves the pull wire mounting elements in opposite linear directions along the longitudinal axis.

11 Claims, 9 Drawing Sheets

(56) References Cited

U.S. PATENT DOCUMENTS

| | | | |
|---|---|---|---|
| 5,409,453 A * | 4/1995 | Lundquist | A61B 10/06 |
| | | | 607/99 |
| 5,480,382 A * | 1/1996 | Hammerslag | A61M 25/0147 |
| | | | 604/95.04 |
| 5,941,849 A * | 8/1999 | Amos, Jr. | A61M 25/0136 |
| | | | 604/95.04 |
| 7,351,222 B2 * | 4/2008 | Sauvageau | A61M 25/0147 |
| | | | 604/95.04 |
| 8,676,290 B2 * | 3/2014 | Tegg | A61M 25/0136 |
| | | | 606/41 |
| 9,138,561 B2 | 9/2015 | Stenzel et al. | |
| 9,247,990 B2 | 2/2016 | Kauphusman et al. | |
| 10,588,744 B2 * | 3/2020 | Rupp | A61F 2/2433 |
| 10,779,807 B2 * | 9/2020 | Xie | A61B 17/0057 |
| 11,890,431 B2 * | 2/2024 | Edminster | A61M 25/0108 |
| 2006/0142694 A1 * | 6/2006 | Bednarek | A61M 25/0136 |
| | | | 604/95.04 |
| 2009/0270896 A1 * | 10/2009 | Sullivan | A61M 1/842 |
| | | | 606/170 |
| 2011/0144576 A1 | 6/2011 | Rothe et al. | |
| 2011/0264074 A1 | 10/2011 | Tegg et al. | |
| 2011/0282176 A1 * | 11/2011 | Tegg | A61M 25/0147 |
| | | | 604/95.04 |
| 2012/0089125 A1 * | 4/2012 | Scheibe | A61M 25/0147 |
| | | | 604/523 |
| 2013/0030519 A1 * | 1/2013 | Tran | A61F 2/958 |
| | | | 623/2.11 |
| 2016/0074625 A1 * | 3/2016 | Furnish | A61M 25/0133 |
| | | | 604/95.04 |
| 2016/0331932 A1 * | 11/2016 | Davies | A61M 25/0147 |
| 2017/0143940 A1 * | 5/2017 | Flygare | A61M 25/0133 |
| 2018/0050195 A1 * | 2/2018 | Knippel | A61N 1/37205 |
| 2018/0256851 A1 * | 9/2018 | Edminster | A61M 25/0108 |
| 2019/0038873 A1 | 2/2019 | Schultheis et al. | |
| 2019/0083748 A1 * | 3/2019 | Khuu | A61M 25/0136 |
| 2019/0083750 A1 * | 3/2019 | Rezac | A61M 25/0136 |
| 2020/0061340 A1 * | 2/2020 | Mixter | A61M 25/0147 |
| 2020/0253635 A1 * | 8/2020 | Stack | A61M 60/135 |
| 2020/0254166 A1 * | 8/2020 | Stack | A61M 25/09 |
| 2020/0345493 A1 * | 11/2020 | Gregg | A61F 2/2436 |
| 2021/0031006 A1 * | 2/2021 | Subramaniam | A61M 25/0147 |

FOREIGN PATENT DOCUMENTS

| | | | | |
|---|---|---|---|---|
| WO | 20180116509 A1 | 6/2018 | | |
| WO | WO-2018116509 A1 * | 6/2018 | ......... | A61M 25/0136 |

OTHER PUBLICATIONS

English machine translation of JP 2018029795, dated Mar. 1, 2018, 25 pages.

English machine translation of WO 20180116509, dated Jun. 28, 2018, 21 pages.

Examination Report dated Mar. 5, 2024, corresponding to Application No. 19 195 025.2-1122, 4 pages.

\* cited by examiner

MEDICAL DEVICE HANDLE FOR ARTICULATION OF A CATHETER

CROSS-REFERENCE TO RELATED APPLICATION

This application claims the benefit of the filing date under 35 U.S.C. § 119(a)-(d) of European Patent Application No. 19195025.2, filed on Sep. 3, 2019.

FIELD OF THE INVENTION

The present invention relates to a medical device handle and, more particularly, to a medical device handle for articulation of a catheter.

BACKGROUND

A number of medical procedures require accessing and visualizing interior regions of a body lumen, for example of the heart. To that end, imaging systems based on a catheter can be used. Furthermore, it is known that intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure in which an artificial valve or valve repair device is guided to the heart through the patient's vasculature.

The distal end of the catheter may be deflected by one or more deflecting mechanisms, which can be achieved by a tension cable, or other mechanisms positioned inside the catheter. Precise control of the distal end of the catheter allows for more reliable and faster positioning of a medical device and/or implant and other improvements in the procedures. Apart from structural heart applications, the catheters are also used for minimally invasive procedures such as neurovascular, coronary, structural heart, peripheral vascular or endoscopic type procedures for gastrointestinal applications or other.

In particular, steering systems are known that cause a distal end of a catheter to move in response to an actuation on the proximal end. For instance, it is known for articulation of catheter distal sections to use steering wires or cables with one end attached proximal to pull wire mounts, the other end anchored at the catheter distal end. In order to allow for an accurate steering of the catheter tip, however, there is still a need for an actuating mechanism that can be fabricated in a particularly simple manner and provides an accurate actuation via the medical device handle.

SUMMARY

A medical device handle for articulation of a catheter includes a housing having a cylindrical shape, a control element at least partly encompassed by the housing, the control element having a pair of cross-cut threads cross-cut in opposing directions around a longitudinal axis of the medical device handle, and a pair of pull wire mounting elements each having a mounting thread engaging with one of the cross-cut threads. The control element is mechanically coupled to each of the pull wire mounting elements via the cross-cut threads and the mounting threads without any additional gear in between. A rotation of the control element around the longitudinal axis moves the pull wire mounting elements in opposite linear directions along the longitudinal axis.

BRIEF DESCRIPTION OF THE DRAWINGS

The invention will now be described by way of example with reference to the accompanying Figures, of which.

DETAILED DESCRIPTION OF THE EMBODIMENT(S)

The accompanying drawings are incorporated into the specification and form a part of the specification to illustrate several embodiments of the present invention. These drawings, together with the description, serve to explain the principles of the invention. The drawings are merely for the purpose of illustrating the examples of how the invention can be made and used, and are not to be construed as limiting the invention to only the illustrated and described embodiments. Furthermore, several aspects of the embodiments may form—individually or in different combinations—solutions according to the present invention. The following described embodiments thus can be considered either alone or in an arbitrary combination thereof. Further features and advantages will become apparent from the following more particular description of the various embodiments of the invention, as illustrated in the accompanying drawings, in which like references refer to like elements.

As used herein, the terms "proximal" and "distal" are to be taken as relative to a user using the disclosed delivery devices. "Proximal" is to be understood as relatively closer to the user and "distal" is to be understood as relatively farther away from the user.

Figure 1:
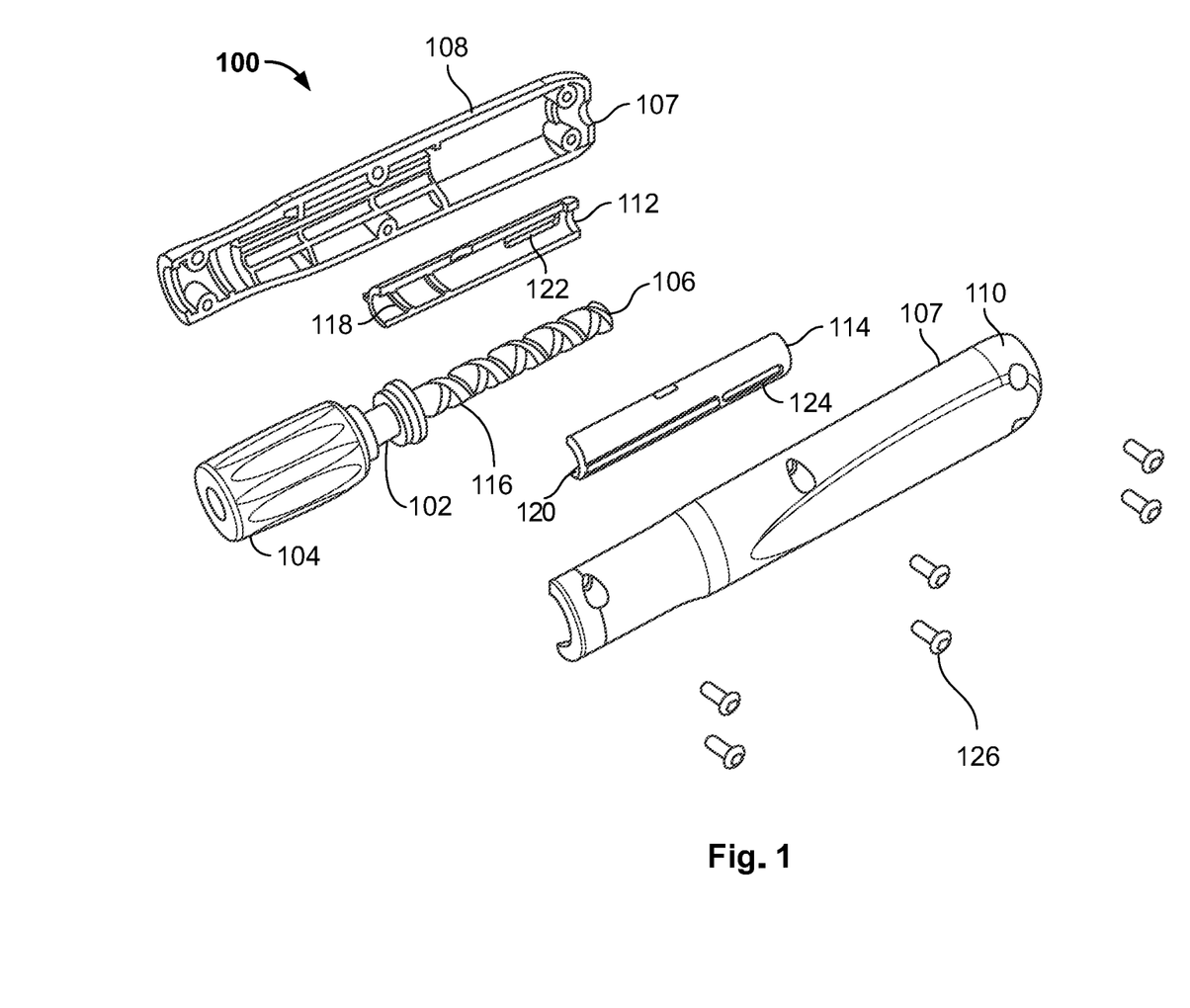
FIG. 1 is an exploded perspective view of a medical device handle according to an embodiment.

A medical device handle 100 according to an embodiment is shown in FIG. 1. The medical device handle 100 comprises a control element 102 with a rotatable adjustment knob 104 and a rotating shaft 106. The rotating shaft 106 has two external cross-cut threads 116 which are cross-cut in opposing directions along a longitudinal axis of the handle 100. The medical device handle 100 can be attached to a proximal end of a catheter 136, shown in FIG. 4, for actuating pull wires which are attached to a distal end of the catheter 136.

By rotating the adjustment knob 104 around a longitudinal axis of the handle 100, the pull wires can be actuated. The control element 102 is rotatable about the longitudinal axis of the handle 100 up to 720 degrees or more. The rotation of the control element 102 can be limited by a stop element 103, shown in FIGS. 2 and 3, that limits the rotation of the control element 102 by abutment of the pull wire mounting elements 112 and 114 with the stop element 103; such a stop element 203 enhances the safety of the handle 100.

For attaching the pull wires, the medical device handle 100 further comprises a first and a second pull wire mounting element 112 and 114, as shown in FIGS. 1-4. The pull wire mounting elements 112 and 114 resemble the shape of a tube which is cut in two halves along its longitudinal axis. The pull wire mounting elements 112 and 114, in the shown embodiment, each have a semi-circular shape. The pull wire mounting elements 112 and 114 together circumferentially surround the rotating shaft 106 of control element 102 from two sides; the pull wire mounting elements 112 and 114 are disposed on sides of the control element 102 opposite to one another in a direction perpendicular to the longitudinal axis. Each pull wire mounting element 112 and 114 has an internal mounting thread 118 and 120 to suit and engage one of the external cross-cut threads 116 of the control element 102. Each pull wire mounting element 112 and 114 has a connector 122 and 124 for connecting a pull wire to the pull wire mounting element 112 and 114.

The control element 102 is mechanically and directly coupled to each of the pull wire mounting elements 112 and 114 via the threads 118, 120 without any additional gear in between. This reduces the number of components necessary such that the medical device handle 100 can be fabricated in a particular cost-efficient way and is less error-prone. The direct coupling allows for a particularly precise manual operation of the pull wire mechanism.

Figure 4:
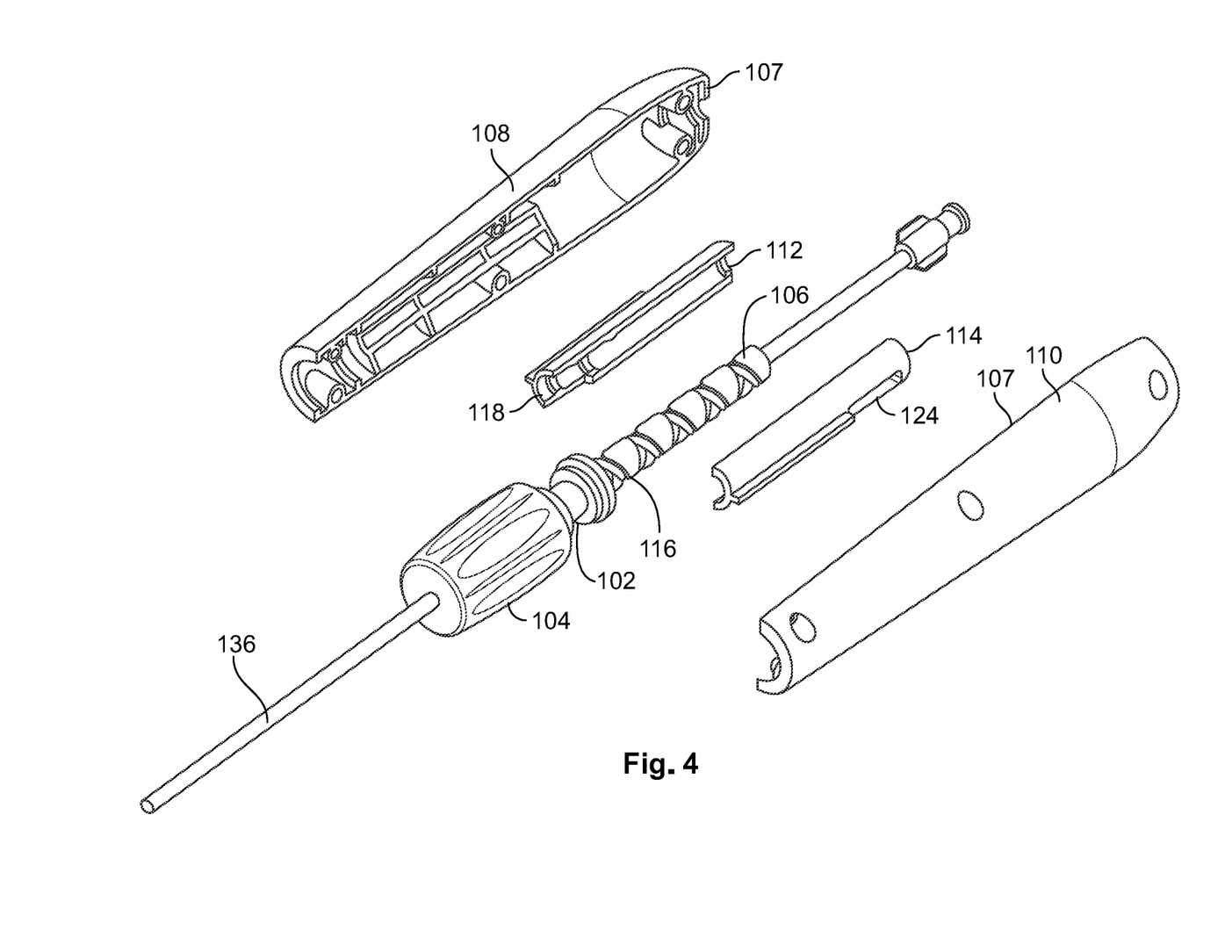
FIG. 4 is an exploded perspective view of the medical device handle with a catheter.

The medical device handle 100 further comprises a housing 107, as shown in FIGS. 1 and 4. The housing 107 at least partly encompasses the control element 102 and the pull wire mounting elements 112 and 114. The housing 107 comprises two halves 108 and 110 which surround the pull wire mounting elements 112 and 114. The two halves 108 and 110 are connected via screws 126. The housing 107 keeps the other elements of the medical device handle 100 together and serves as the actual handle to hold the medical device handle 100.

Figure 2:
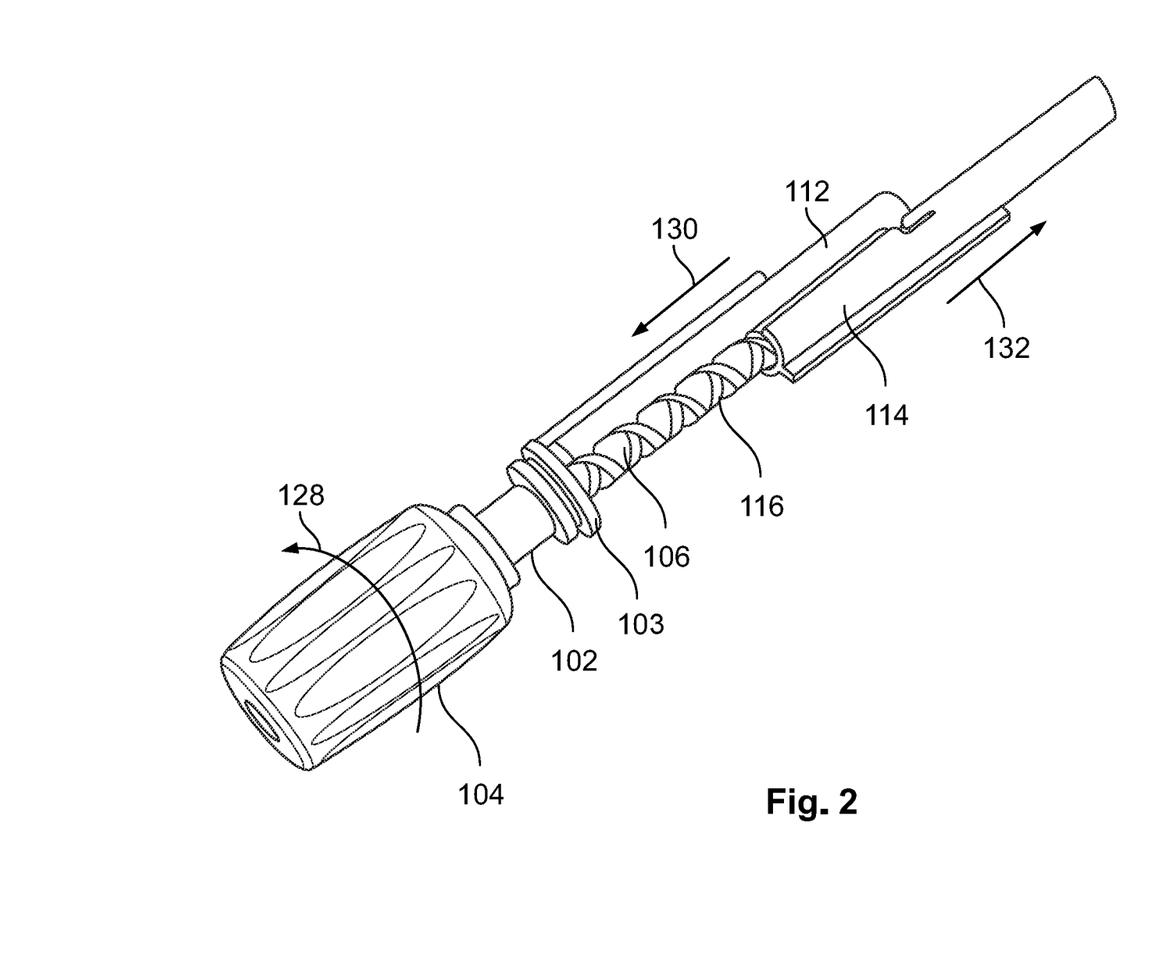
FIG. 2 is a perspective view of rotating a shaft of the medical device handle counterclockwise.
Figure 3:
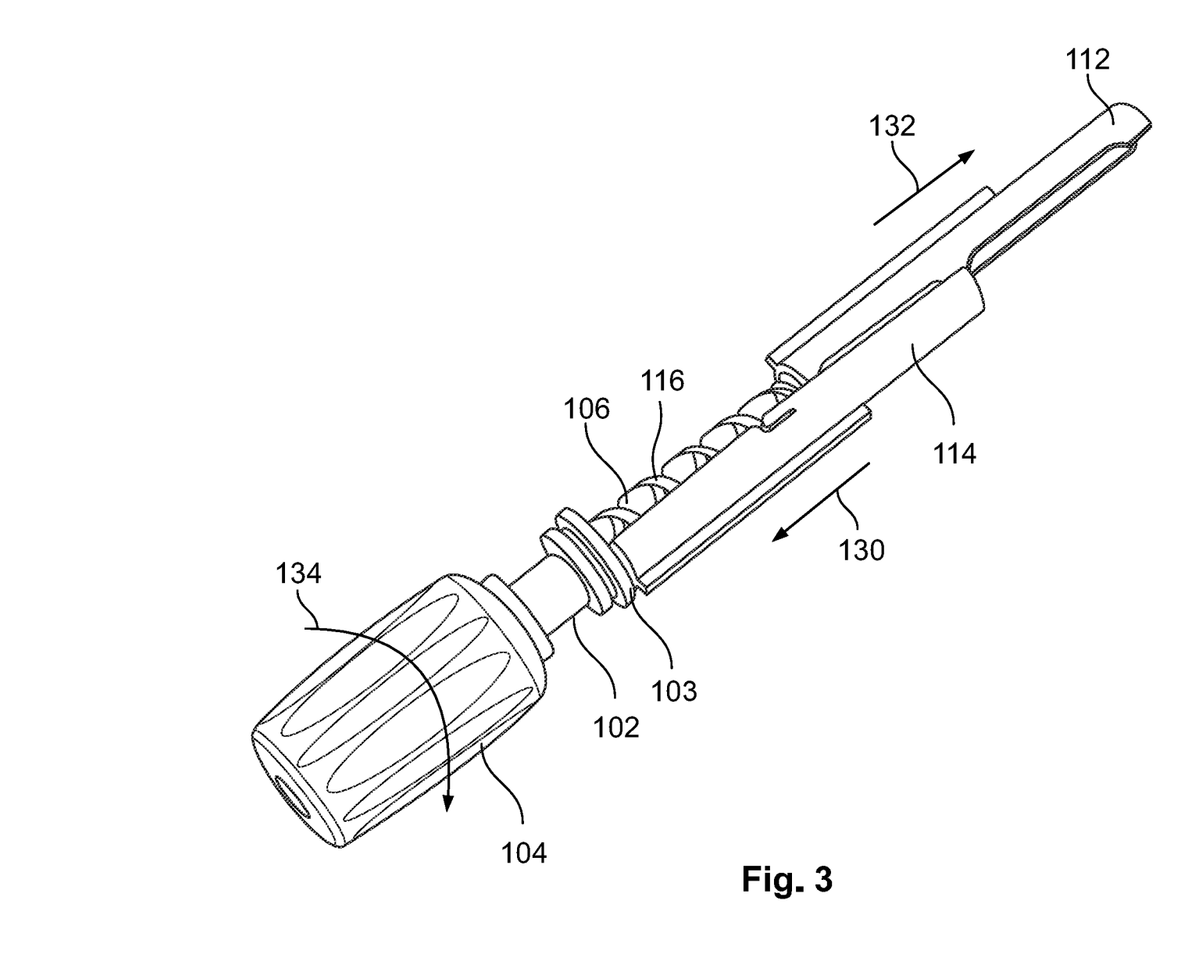
FIG. 3 is a perspective view of rotating the shaft of the medical device handle clockwise.

As shown in FIG. 2, rotating the control element 102 in a counterclockwise direction 128 causes the pull wire mounting elements 112 and 114 to move in opposite linear directions 130 and 132 along the longitudinal axis of the medical device handle 100. As shown in FIG. 3, rotating the control element 102 in a clockwise direction 134 causes the pull wire mounting elements 112 and 114 to move in interchanged opposite linear directions 132 and 130 along the longitudinal axis of the medical device handle 100. The rotation of the control element 102 moves at least one of the pull wire mounting elements 112 and 114 to extend beyond an end of the control element 102 along the longitudinal axis. Directions such as "left" and "right" and "clockwise" and "counterclockwise" refer to the standpoint of a person operating the device handle 100.

As shown in FIG. 4, the medical device handle 100 can comprise an elongate catheter 136 which extends from the housing 107. The pull wire mounting elements 112 and 114 are connected to the catheter 136 via pull wires at connectors 122 and 124. Accordingly, the position of the catheter 136 can be controlled by rotating the control element 102; the pull wire mounting elements 112 and 114 allow for steering a tip of the catheter 136. Since the pull wire mounting elements 112 and 114 are moved in opposite linear directions, the tension of the longer side of the pull wires can be reduced. In an embodiment, a position of the pull wire mounting elements 112 and 114 can be selectively locked by a locking mechanism movable between a locked and an unlocked position.

Figure 5:
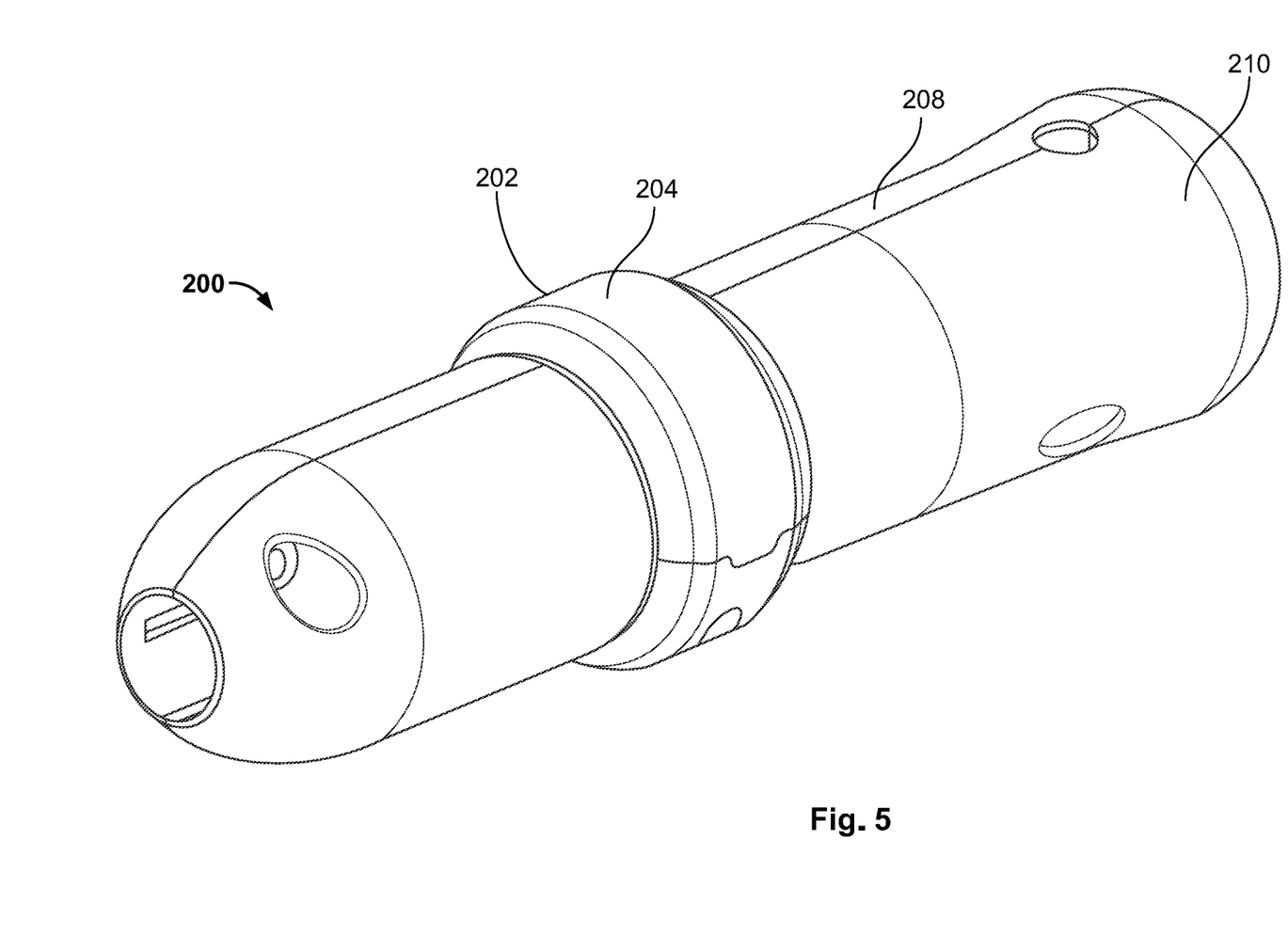
FIG. 5 is a perspective view of a medical device handle according to another embodiment.
Figure 6:
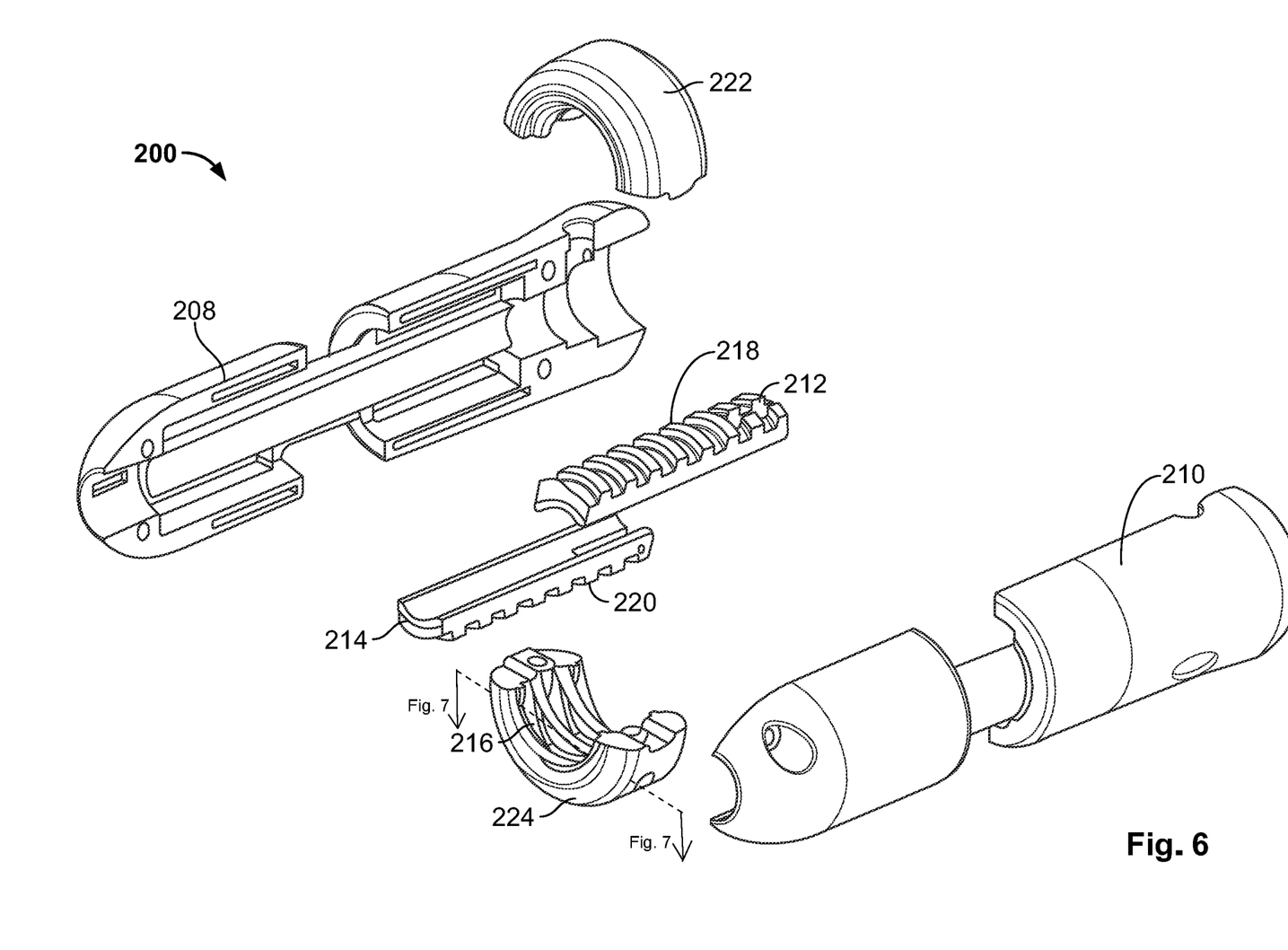
FIG. 6 is an exploded perspective view of the medical device handle of FIG. 5.

A medical device handle 200 according to another embodiment is shown in FIGS. 5 and 6. Like reference numbers refer to like elements, and primarily the differences of the medical device handle 200 with respect to the medical device handle 100 will be described in detail herein.

Figure 7:
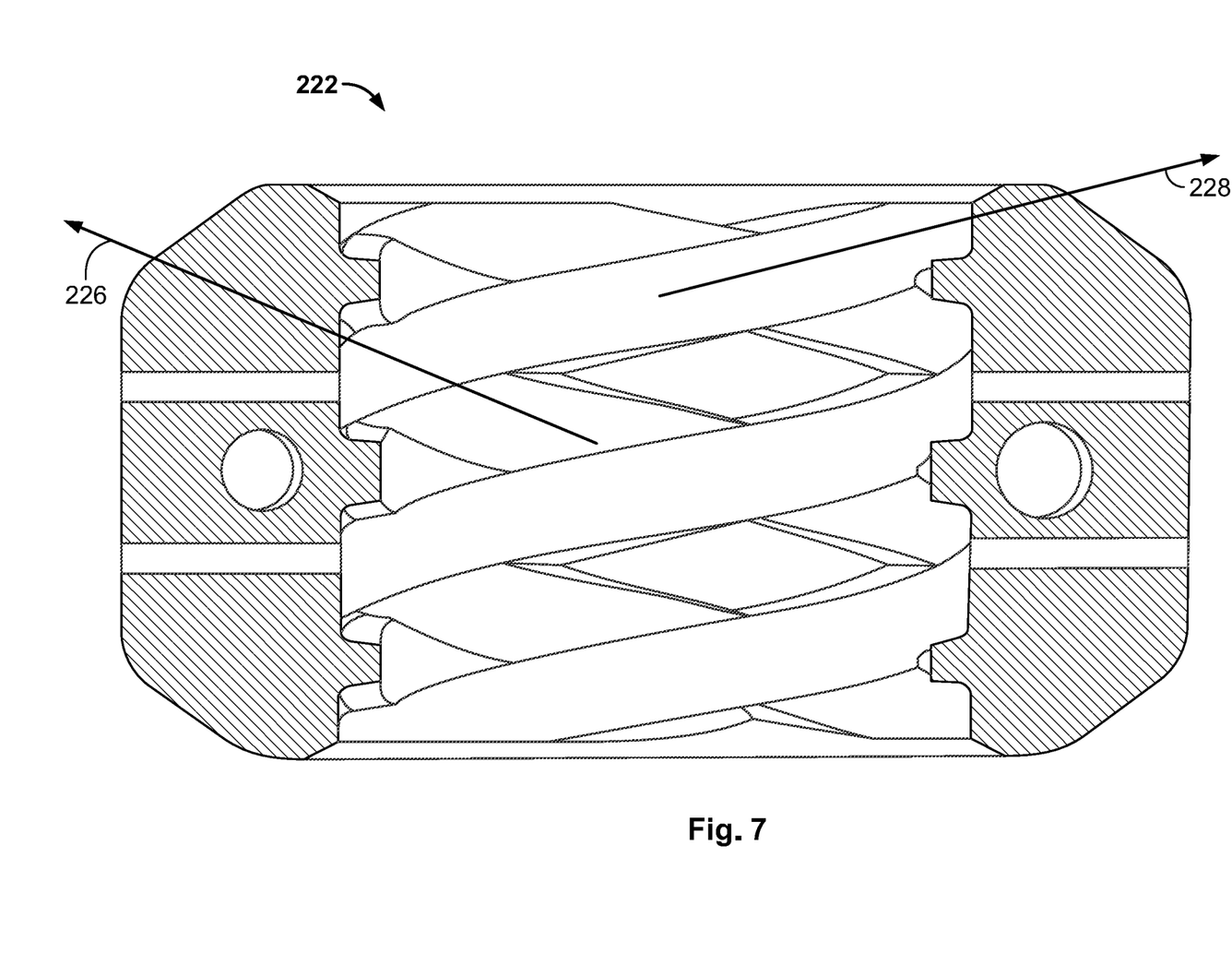
FIG. 7 is a sectional schematic diagram of a control element of the medical device handle of FIG. 5 with two internal threads cross cut in opposing directions, taken along the section line 7-7 in FIG. 6.

The medical device handle 200 as shown in FIGS. 5 and 6, comprises a control element 202 that is a rotating component formed as an adjustment knob 204. The adjustment knob 204 has internal cross-cut threads 216 on a first half 222 of the adjustment knob 204 and on a second half 224 of the adjustment knob 204 that is connectable to the first half 222. The internal threads 216 are two threads 226 and 228 that are cross-cut in opposite directions, as shown in FIG. 7.

The medical device handle 200 has first and second pull wire mounting elements 212 and 214 having an external mounting thread 218 and 220 to suit one of the crosscut threads 216. The control element 202 has internal instead of external threads, as shown in FIG. 6, whereas the pull wire mounting elements 212 and 214 have external 218 and 220 instead of internal threads. The medical device handle 200 further includes a housing including a first half shell 208 and a second half shell 210 connectable to the first half shell 208.

Figure 8:
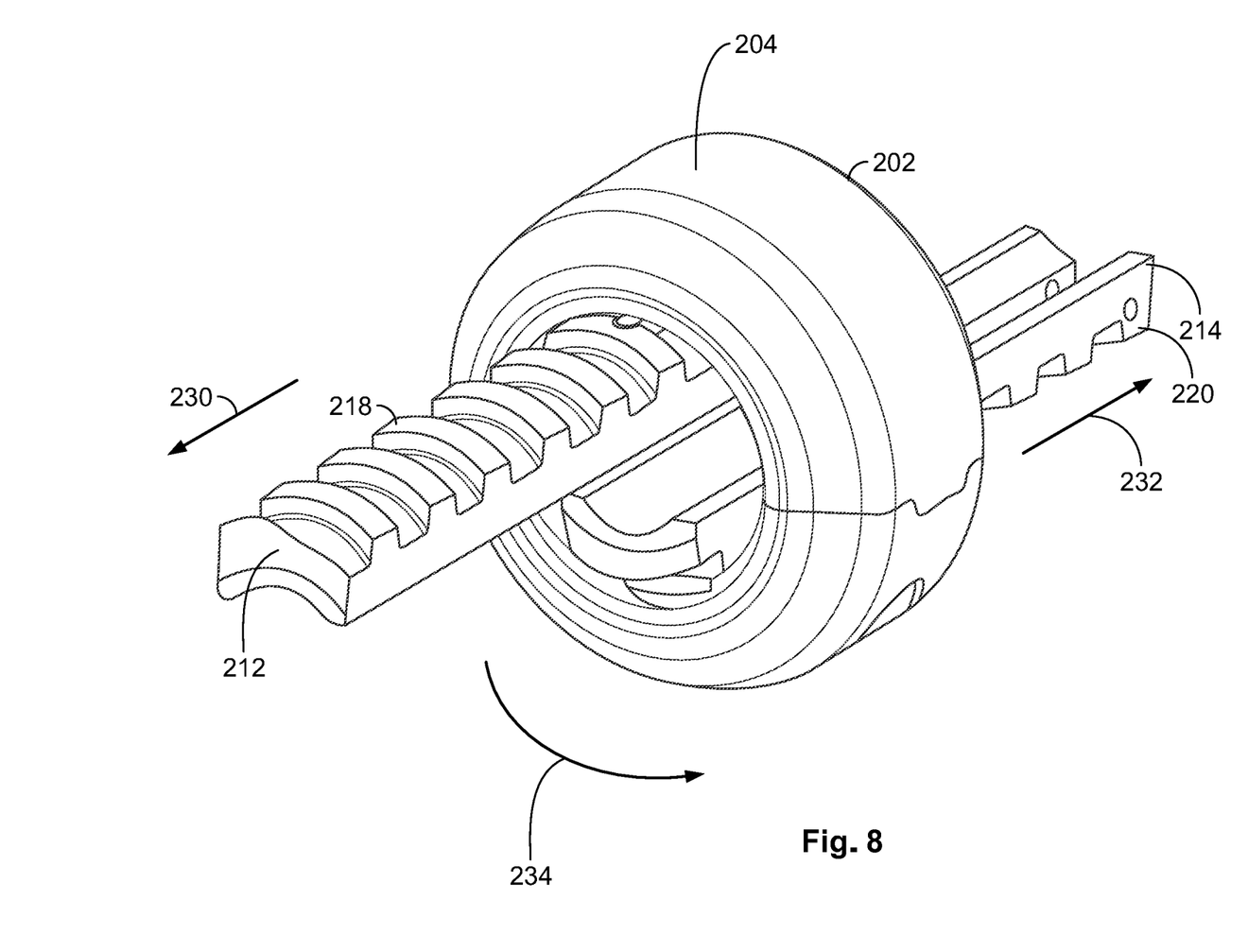
FIG. 8 is a perspective view of rotating a shaft of the medical device handle of FIG. 5 counterclockwise.
Figure 9:
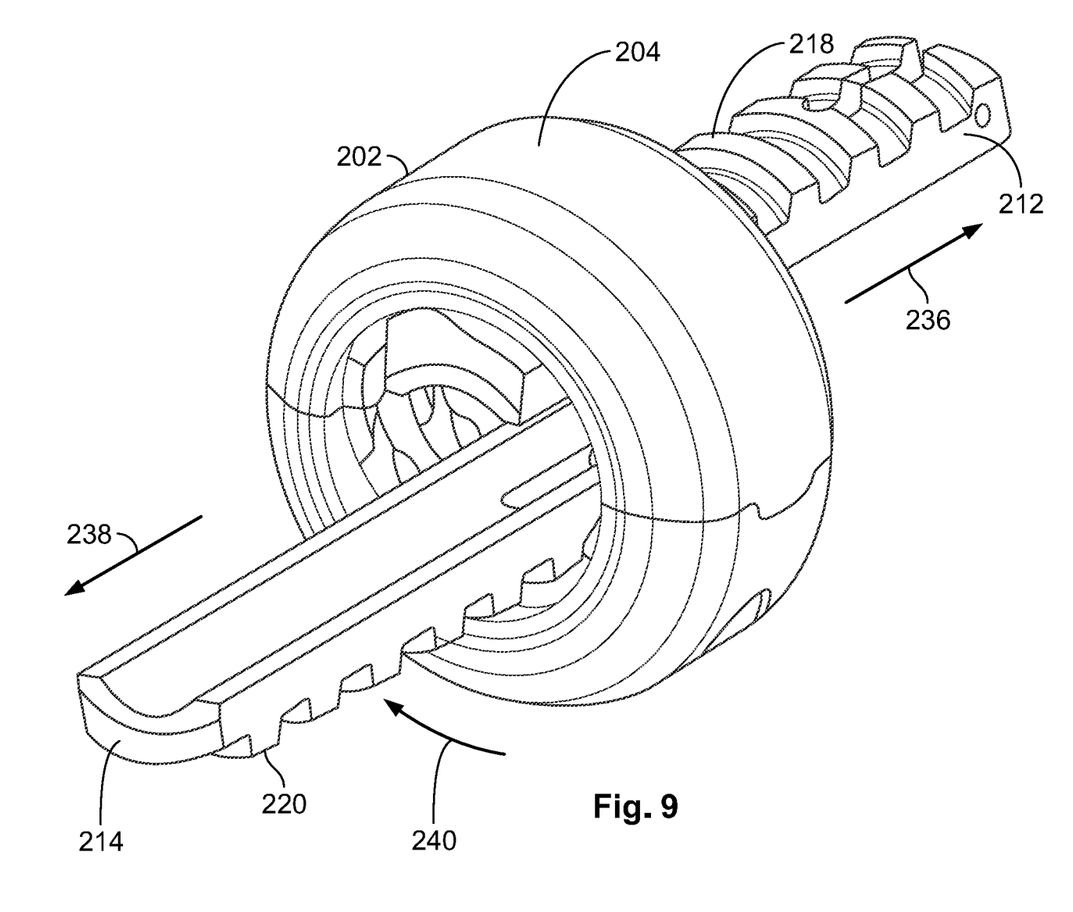
FIG. 9 is a perspective view of rotating a shaft of the medical device handle of FIG. 5 clockwise.

As shown in FIG. 8, rotating the adjustment knob 204 in a counterclockwise direction 234 causes the pull wire mounting elements 212 and 214 to move in opposite linear directions 230 and 232 along the longitudinal axis of the medical device handle 200. As shown in FIG. 9, rotating the adjustment knob 204 in a clockwise direction 240 causes the pull wire mounting elements 212 and 214 to move in interchanged opposite linear directions 236 and 238 along the longitudinal axis of the medical device handle 100. Therefore, the tension of the longer side of the pull wires can be reduced. Again, there is no additional gear between the control element 102 and the pull wire mounting elements 212 and 214, which reduces the number of components necessary such that the medical device handle 100 can be fabricated in a particular cost-efficient way and is less error-prone.

The present invention also relates to a corresponding method of assembling a medical device handle 100, 200 for articulation of a catheter. This method comprises providing a control element 102, 202 having two threads 116, 216 which are cross-cut in opposing directions around a longitudinal axis of the control element 102, 202; providing two pull wire mounting elements 112, 114, 212, 214, each having a thread 118, 120, 218, 220 to engage with one of the cross-cut threads 112, 216 of the control element 102, 202; and providing a cylindrically shaped housing 108, 110, 208, 210. The housing 108, 110, 208, 210 is mounted such that it at least partly encompasses said elements. Moreover, the method comprises mechanically coupling the control element 102, 202 to each of the pull wire mounting elements 112, 114, 212, 214 via the threads without any additional gear in between.

The method can also comprise crosscutting the threads 116, 216 into the external surface of the control element 102 or into the internal surface of the control element 202. Moreover, the method can comprise connecting the pull wire mounting elements 112, 114, 212, 214 to pull wires.

The handle 100, 200 allows for releasing tension of the pull wires and for minimizing the number of components necessary, such that the handle 100, 200 can be fabricated in a particularly cost-efficient way and is less error-prone. The advantage of this solution can be seen in providing a particularly simple, but at the same time accurate steering system.

What is claimed is:

1. A medical device handle for articulation of a catheter, comprising:
   a housing having a cylindrical shape;
   a control element at least partly encompassed by the housing, the control element having a pair of cross-cut threads cross-cut in opposing directions around a longitudinal axis of the medical device handle;
   a pair of pull wire mounting elements each having a mounting thread engaging with one of the cross-cut threads, the pull wire mounting elements are disposed on sides of the control element opposite to one another in a direction perpendicular to the longitudinal axis, the control element is mechanically coupled to each of the pull wire mounting elements via the cross-cut threads and the mounting threads without any additional gear in between, a rotation of the control element around the longitudinal axis moves the pull wire mounting elements in opposite linear directions along the longitudinal axis; and
   a stop element of the control element that limits rotation of the control element by abutment of the pull wire mounting elements with the control element, the stop element limits rotation of the control element by abutment of the pull wire mounting elements with a rotational portion of the control element.

2. The medical device handle of claim 1, wherein the housing has an elongate catheter extending therefrom.

3. The medical device handle of claim 2, wherein the pull wire mounting elements are connectable to pull wires that allow for steering a tip of the elongate catheter.

4. The medical device handle of claim 1, wherein the control element is a rotating shaft with a pair of external threads formed as the cross-cut threads.

5. The medical device handle of claim 1, wherein the control element is rotatable up to 720 degrees about the longitudinal axis.

6. The medical device handle of claim 1, wherein the pull wire mounting elements each have a semi-circular shape extending around the control element.

7. The medical device handle of claim 6, wherein the pull wire mounting elements together form a tubular shape cut in two halves and together circumferentially surround the control element.

8. The medical device handle of claim 1, wherein the rotation of the control element moves at least one of the pull wire mounting elements to extend beyond an end of the control element along the longitudinal axis.

9. A method of assembling a medical device handle for articulation of a catheter, comprising:
   providing a control element having a pair of cross-cut threads cross-cut in opposing directions around a longitudinal axis of the control element;
   providing a pair of pull wire mounting elements each having a mounting thread engaging with one of the cross-cut threads;
   providing a housing having a cylindrical shape;
   mounting the housing to at least partly encompass the pull wire mounting elements and the control element;
   mechanically coupling the control element to each of the pull wire mounting elements via the cross-cut threads and the mounting threads without any additional gear in between, the pull wire mounting elements are disposed on sides of the control element opposite to one another in a direction perpendicular to the longitudinal axis; and
   providing a stop element of the control element that limits rotation of the control element by abutment of the pull wire mounting elements with the control element, the stop element limits rotation of the control element by abutment of the pull wire mounting elements with a rotational portion of the control element.

10. The method of claim 9, wherein the cross-cut threads are cross-cut into an external surface of the control element.

11. The method of claim 9, wherein mechanically coupling comprises coupling such that rotating the control element around the longitudinal axis moves the pull wire mounting elements in opposite linear directions.

* * * * *